United States Patent [19]

Dekiouk et al.

[11] Patent Number: 5,234,874

[45] Date of Patent: Aug. 10, 1993

[54] ATTRITION-RESISTANT CATALYST SYSTEM AND ITS APPLICATION TO THE OXIDATIVE DEHYDROGENATION OF SATURATED CARBOXYLIC ACIDS, ESPECIALLY IN ENTRAINED-BED REACTORS

[75] Inventors: Mohammed Dekiouk, Woustviller; Gérard Hecquet, Bethune; Stanislas Pietrzyk, Mons en Baroeul, all of France

[73] Assignee: Atochem, Paris, France

[21] Appl. No.: 681,683

[22] Filed: Apr. 8, 1991

[30] Foreign Application Priority Data

Apr. 6, 1990 [FR] France ................. 90 04417

[51] Int. Cl.$^5$ ................. B01J 29/04; B01J 27/185
[52] U.S. Cl. ................. 502/74; 502/213
[58] Field of Search ................. 502/74, 66, 213

[56] References Cited

U.S. PATENT DOCUMENTS

| | | | |
|---|---|---|---|
| 3,862,910 | 1/1975 | Cichowski | 252/435 |
| 4,483,936 | 11/1984 | Liu et al. | 502/74 |
| 4,556,645 | 12/1985 | Coughlin et al. | 502/74 |
| 4,585,748 | 4/1986 | Usui et al. | 502/66 |

FOREIGN PATENT DOCUMENTS

| | | |
|---|---|---|
| 0148048 | 7/1985 | European Pat. Off. . |
| 0158694 | 10/1985 | European Pat. Off. . |
| 0188841 | 7/1986 | European Pat. Off. . |
| 0217428 | 4/1987 | European Pat. Off. . |

*Primary Examiner*—Carl F. Dees
*Attorney, Agent, or Firm*—Millen, White, Zelano & Branigan

[57] ABSTRACT

For the oxidative dehydrogenation of saturated carboxylic acids to form $\alpha,\beta$-unsaturated carboxylic acids, saturated acids are contacted with a gas containing molecular oxygen and, where appropriate, an inert diluent gas, in the vapor phase, at a reaction temperature of 250° to 600° C., in the presence of a catalyst system comprising a non-supported catalyst of the formula $FeP_xMe_yO_z$, wherein: Me is at least one of the following elements: Li, Na, K,, Rb, Cs, Mg, Ca, Sr and Ba; x has a value from 0.2 to 3.0; y has a value from 0.01 to 0.2; and z is the quantity of oxygen bonded to the other elements and corresponding to their oxidation state, in an entrained-bed reactor and, where appropriate, in the presence of steam in a molar ratio to the saturated acid not exceeding 0.5. The catalyst is beneficially associated with at least one zeolite, preferably in a concentration sufficient to improve the attrition resistance of the catalyst, e.g., in an amount by weight of about 1–10% of the catalyst.

11 Claims, No Drawings

ATTRITION-RESISTANT CATALYST SYSTEM AND ITS APPLICATION TO THE OXIDATIVE DEHYDROGENATION OF SATURATED CARBOXYLIC ACIDS, ESPECIALLY IN ENTRAINED-BED REACTORS

BACKGROUND OF THE INVENTION

The present invention relates to an attrition-resistant catalyst system based on phosphorus and iron oxides, with a view to the gas phase oxidative dehydrogenation of saturated carboxylic acids to corresponding unsaturated acids, in particular with a view to the oxidative dehydrogenation of isobutyric acid to methacrylic acid in an entrained-bed reactor.

A material substance with catalytic activity for such a catalyst system has already been described in Patent FR-A-2,497,795 and is denoted by the general formula $FeP_xMe_yO_z$, in which:

Me denotes at least one of the following elements: Li, Na, K, Rb, Cs, Mg, Ca, Sr and Ba, x has a value from 0.2 to 3.0, y has a value from 0.01 to 0.2, and z is the quantity of oxygen bonded to the other elements and corresponding to their oxidation state.

Catalysts of this type take the form, inter alia, of a bulk solid. The term "bulk solid" in the context of this invention is meant to define a non-supported catalyst. As a general rule the preparation is carried out in an aqueous medium, the oxides of iron, phosphorus and of the metal Me being prepared by evaporating down an iron salt, a salt of the metal Me and orthophosphoric acid.

In accordance with Patent FR-a-2,497,795, the oxidative dehydrogenation reaction is carried out in a stationary-bed reactor. The stationary bed consists of a motionless compact charge of catalyst particles stacked in a tube. The catalyst particle size (a few millimeters in diameter) is such that it must reduce the pressure drop to a minimum but it thus involves a limitation on diffusion. To improve the yield of the desired product, the reaction is carried out in the presence of steam in a molar ratio to the substrate of approximately 1 to 74, preferably 10 to 30. Under these conditions the conversions and the selectivities are generally high, given that the flow of gas approximates plug flow and that the contact time can be controlled accurately. Thus, isobutyric acid conversion may be up to 98% and the selectivity for methacrylic acid up to 70%. Nevertheless, with an exothermic catalytic reaction, as is the case with the oxidative dehydrogenation of saturated carboxylic acids, hot spots sometimes appear, and these affect catalyst performance, especially by modifying the selectivities. It is then necessary to resort to catalyst replacement when the performance is affected. In addition, the presence of large quantities of water makes the separation of the water after reaction very costly.

It would therefore be advantageous to be able to conduct such reactions in the presence of very small quantities of water, for example in a so-called entrained-bed or transported-bed or pneumatic-transport reactor. Such reactors comprise an upward-flow column in which the gaseous reactant feed and the catalyst suspended in the latter travel concurrently upwards. The product leaving at the top of the column is separated from the catalyst in a device of the cyclone type. The catalyst is then generally sent to the top part of a fluidized-bed regeneration column in which a regenerating gas circulates; it leaves the regenerating column in the bottom part thereof, from which it is sent back to the bottom of the upward-flow column.

Such an entrained-bed reactor has the following advantages:

on the one hand, plug flow in the case of the gas and the solid, permitting an accurate control of the residence time of the gaseous mass and of the solid phase, and on the other hand, it avoids the reaction zone being short-circuited by bubbles, as happens in the case of fluidized-bed reactors, possibility of reducing the water content in the reaction section formed by the upward-flow column and of regenerating the catalyst with the aid of an aqueous gas stream, especially a mixture of steam and oxygen which may also contain an inert gas such as nitrogen, as well as a reactant which compensates for any loss of phosphorus from the catalyst during the reaction cycle, and, lastly, very low water consumption in the reaction section.

In addition, temperature control is efficient in the case of exothermic reactions, owing to the fact that the solid particles which are carried over, because of their high heat capacity, remove the heat of the reaction. Above all, however, the crucial advantage is the possibility of accurately separating the two stages of the catalyst operation, namely the reduction of the solid catalyst in the first step and, in a second step, its oxidation and its rehydration with a view to regeneration. oxidation and its rehydration with a view to regeneration.

A procedure in accordance with the teaching of Patent EP-A-263,005 may be followed to regenerate the catalyst.

Nevertheless, a reactor of this type imposes some constraints: thus, the catalyst must resist attrition which results from the impact of the particles on each other or on the internal walls.

SUMMARY OF THE INVENTION

It has now been found that it is possible to enjoy the abovementioned advantages of entrained-bed reactors for the oxidative dehydrogenation of saturated carboxylic acids, by virtue of a bulk catalyst of the type referred to above, and that the use of this reaction in an entrained-bed reactor can be improved if the catalyst is modified to enable it to resist attrition, by the incorporation of a sufficient amount of a zeolite therein.

One aspect of the present invention is therefore to provide firstly a catalyst system comprising the catalyst of general formula $FeP_xMe_yO_z$, in which Me, x, y and z are as defined above, characterized in that it is in a bulk solids form, i.e., non-supported, and that it is associated with at least one zeolite.

Zeolites are crystalline aluminosilicates of natural and synthetic origin. Their one-, two- or three-dimensional structure consists of a stack of $AlO_4$ and $SiO_4$ tetrahedra, two tetrahedra being linked together only by a single oxygen bridge. Since aluminum is trivalent, the $AlO_4$ tetrahedron carries a negative charge compensated by a cation which can vary very widely in its nature ($Na^+$, $K^+$, $Ca^{++}$, $Mg^{++}$, and the like, organic cations, and the like). Zeolites are denoted by the unitary empirical 2), and $nx=y$, $y=1$, $1 \leq z/y \leq 6$, and $3 \leq w \leq 5$, and they have a microporous structure which is close to that of the molecules treated in size. A zeolite may be chosen which is natural or synthetic, exhibiting pores with an opening of generally between 0.3 and 1.3 nm, and/or with a crystallinity of at least 90%, such as, for example, mordenite, and/or with a mean particle size chosen especially between 30 and 100 μm, preferably between 40 and 60 μm, and/or exhibiting a specific surface which is generally between 50 and 300 m$^2$/g, preferably between 100 and 200 m$^2$/g.

The fraction of zeolite in the catalyst system generally represents approximately 1 to 10% by weight of the actual catalyst. By "actual catalyst" is meant the catalyst without the zeolite.

The specific surface of the catalyst system according to the invention is generally between approximately 4 and 10 m$^2$/g.

This catalyst system is especially in the form of particles which have a dimension of between approximately 50 and 400 μm.

Such a catalyst system can be prepared by distillation, at atmospheric pressure or under a vacuum (for example, on the order of $2\times10^4$ to $10^5$ Pa) of an aqueous solution of phosphoric acid containing an iron compound (such as Fe(NO$_3$)$_3$.9H$_2$O) and a compound of the metal Me, as well as a quantity ranging from approximately 60 to 90%, relative to the weight of the aqueous solution of phosphoric acid, of the zeolite, to remove an aqueous acidic liquor, followed by evaporation or drying, calcination, milling and screening.

These latter stages are well known to a person skilled in the art. Examples include but are not limited to: an evaporation at approximately 120° C. for approximately 16-24 hours or at approximately 180° C. for approximately 4-8 hours, and a calcination at approximately 400°-500° C. for approximately 6-24 hours.

Another aspect of the present invention is to provide a process for the oxidative dehydrogenation of saturated carboxylic acids to form α,β-unsaturated carboxylic acids, this process comprising bringing the said saturated acids into contact with molecular oxygen or a gas containing oxygen and, where appropriate, an inert diluent gas in the vapor phase, at a reaction temperature of approximately 250°-600° C., preferably 350° to 450° C., in the presence of a catalyst system comprising a catalyst of the general formula FeP$_x$Me$_y$O$_z$ in which x, y, z and Me have the abovementioned meanings, in an entrained-bed reactor and, where appropriate, the catalyst system may be preferably modified by the incorporation of a zeolite such as described above, with a view to improving its attrition resistance.

The operating conditions in the upward-flow column of the entrained-bed reactor are generally as follows: the charge sent into the reactor comprises a generally preheated gaseous mixture of saturated acid, molecular oxygen to the saturated acid is between 0.2 and 20, preferably approximately between 0.5 and 2. When steam is present in the charge sent into the reactor, the molar ratio (not exceeding 0.5) shown above is obviously to be understood to exclude the quantity of water which is generated, as is well known, by the actual oxidative dehydrogenation reaction, the contact time in the upward-flow column is preferably chosen between 0.1 and 50 seconds. It is imperative that the gas velocity must be higher than the terminal free-fall velocity of the catalyst, the calculation of the latter being within the reach of a person skilled in the art.

The volumetric concentration of the catalyst system in relation to the gas stream is generally between 0.1 and 15%, preferably approximately between 1 and 5%.

The operating conditions in the fluidized-bed regenerating column are generally as follows: the fluidized-bed is charged with a mass of catalyst; this charge is brought into contact with a gas stream made up of air, water an inert gas, maintained at a temperature of approximately 300° C. to 500° C., and intended to control the oxidation-reduction state of the catalyst before it is injected into the reaction section. The volumetric content of H$_2$O in the gas stream is generally approximately between 1 and 75%.

Upon further study of the specification and appended claims, further objects and advantages of this invention will become apparent to those skilled in the art.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application France 90 04417, filed Apr. 6, 1990, are hereby incorporated by reference.

EXAMPLES

Example 1: Preparation of a catalyst according to the invention of bulk composition FeP$_{1.23}$Cs$_{0.15}$ Using the necessary quantities, cesium nitrate (CsNO$_3$.H$_2$O) is dissolved in water at 40° C. and iron nitrate (Fe(NO$_3$)$_3$.9H$_2$O) is then added to the solution with stirring. This solution is stirred overnight at room temperature.

In parallel, a solution of 85% H$_3$PO$_4$ is stirred with 3%, relative to the weight of the catalyst oxides, of zeolite Y (Al/Si=0.524, mean diameter of 50 μm, specific surface: 115 m$^2$/g) supplied by the Institut Francais du Pétrole under reference DA 250.

The two solutions are mixed in a round bottom flask with sufficient stirring for homogenization. Next, an evaporation at atmospheric pressure and at a temperature on the order of 115° C. is carried out, with removal of a solution of nitric acid whose volume is on the order of 1.5 l in the case of a starting volume of 8 l.

The solutions are distributed into various porcelain trays which are placed in an oven for a period of one night at 120° C. and then for 8 hours at 180° C.

The cake is then calcined in air for 16 hours at 460° C.; it is crushed and milled to reduce the catalyst to a suitable size (75-150 μm).

The characteristics of this catalyst are as follows:
specific surface of 6 m$^2$/g
mean diameter = 190 μm Example 2

The procedure followed is as in Example 1 to obtain a catalyst of the same bulk formula, except that its specific surface is 5 m$^2$/g.

Comparative Example 3

The procedure followed is as in Example 1, the zeolite being replaced with tetraethyl orthosilicate in a proportion of 3% relative to the quantity of 85%

$H_3PO_4$. The gel is obtained after evaporation. The specific surface of the catalyst obtained is 20 m²/g.

Comparative Example 4

The procedure followed is as in Example 1, 90% of the zeolite being employed in relation to the quantity of 85% $H_3PO_4$.

Comparative Example 5

The procedure followed is as in Example 1, except that the zeolite is replaced with the same quantity of colloidal silica (Ludox) and that after the evaporation at 120° C. overnight and at 180° C. for 8 hours, a milling and a pelleting with carbon are performed, followed by calcination for 16 hours at 460° C.

The specific surface of this catalyst is 5 m²/g.

Example 6: Estimation of attrition

The attrition test marketed by the Géoméchanique Company at Rueil-Malmaison was performed on the catalyst of Example 1 and 2 and Comparative Examples 3 to 5.

The attrition speeds are based on the production for 1 hour of fine particles which are smaller than a given size and are defined by the formula:

$$\frac{\text{final \% of fines} < s - \text{initial \% } < s}{\text{initial \% of fines} < s} \times 100 \, h^{-1}$$

The results obtained are collected in Table I which follows for fractions smaller than 50 μm and 90 μm respectively.

TABLE I

| Example | s < 50 μm | s < 90 μm |
|---------|-----------|-----------|
| 1       | 3.6       | 2.5       |
| Comp. 2 | 15.9      | 10.1      |
| Comp. 3 | 13.0      | n.d       |
| Comp. 4 | 10.4      | 6.7       | n.d. = not determined

From the evidence in Table I it follows that the catalyst which has the best attrition resistance is that of Example 1 according to the invention.

Examples 7 to 12: Dehydrogenation reaction of isobutyric acid (IBA) to methacrylic acid in an entrained-bed reactor The reactor comprises a heated upright column (or reaction section) made of stainless steel, with an internal diameter of 20 mm, a wall thickness of 3 mm, and a height of 2.8 m. The gas-solid separation at the outlet of the said upward-flow column is carried out in a cyclone. The regenerating column comprises a heated fluidized bed whose height/diameter ratio is set at 2.

Liquid isobutyric acid in an oxygen/nitrogen mixture is injected into a vaporizer filled with quartz packing in order to homogenize and vaporize at a temperature which is lower than 350° C. to avoid the combustion of isobutyric acid. The desired oxygen content in the gas mixture is obtained by diluting air in nitrogen, each of the flow rates being monitored by mass flow meters.

The above mixture is injected at approximately 350° C. into the upward-flow column, which is maintained at a temperature of 415° C. In this column, the mixture travels upwards concurrently with the catalyst system of Example 1, which originates from the fluidized bed.

For each of these examples, the total flow rate of the gas stream in the upward-flow column, the molar percentage of isobutyric acid and the $O_2$/isobutyric acid molar ratio in the upward-flow column are shown in Table II below.

The stream leaving the upward-flow column is sent to a cyclone in order to separate off the catalyst system, which is then regenerated. To this end, the fluidized bed is charged with a mass of this catalyst, which is brought into contact with a gas stream, maintained at a temperature of 450° C., and consisting essentially of air, water and nitrogen, to which 100 ppm of triethyl phosphate have been added to compensate for any loss of phosphorus from the catalyst during the reaction cycle. The overall flow rate of this gas stream and the water flow rate are also shown in Table II.

When operating under the conditions which have just been described, both a high isobutyric acid conversion and high selectivity for methacrylic acid are obtained.

TABLE II

| Example | Upward-flow column total flow rate (mol/h) | Mol % of AIB in upward-flow column | $O_2$/AIB molar ratio in upward column | Total fluidization flow rate (mol/h) | Water Flow rate (mol/h) in fluidization (regeneration) |
|---------|---|------|------|--------|------|
| 7  | 83    | 5.37 | 1.26 | 124.3  | 20.6 |
| 8  | 85    | 1.91 | 0.82 | 109.3  | 0    |
| 9  | 85    | 1.91 | 0.82 | 70.9   | 0    |
| 10 | 85    | 1.91 | 0.82 | 117.10 | 8.1  |
| 11 | 103.6 | 4.93 | 0.3  | 85.6   | 0    |
| 12 | 103.6 | 4.93 | 0.3  | 168.3  | 82.8 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A catalyst system comprising a catalyst of formula $FeP_xMe_yO_z$, wherein
   Me is at least one of the following elements: Li, Na, K, Rb, Cs, Mg, Ca, Sr and Ba,
   x has a value from 0.2 to 3.0,
   y has a value from 0.01 to 0.2, and
   z is the quantity of oxygen bonded to the other elements and corresponding to their oxidation state, said catalyst being a non-supported catalyst and further comprising a sufficient amount of at least one zeolite to improve attrition-resistance of the catalyst.

2. A catalyst system according to claim 1, wherein said zeolite has pores of a diameter of between 0.3 and 1.3 nm, and/or a crystallinity of at least 90% and/or a mean particle size of 30 to 100 μm and/or a specific surface of between 50 and 300 m²/g.

3. A catalyst system according to claim 1, wherein zeolite represents 1 to 10% by weight of said catalyst.

4. A catalyst system according to claim 1 having a specific surface of between 4 and 10 m$^2$/g.

5. A catalyst system according to claim 1 having a particle size of between 50 and 400 μm.

6. A catalyst system according to claim 1, wherein said zeolite has pores of a diameter of between 0.3 and 1.3 nm, a crystallinity of at least 90%, a mean particle size of 30 to 100 μm, and a specific surface of between 50 and 300 m$^2$/g.

7. A catalyst system according to claim 6, wherein zeolite represents 1 to 10% by weight of the actual catalyst.

8. A catalyst system according to claim 7 having a specific surface of between 4 and 10 m$^2$/g.

9. A catalyst system according to claim 8 having a particle size of between 50 and 400 μm.

10. A catalyst system according to claim 1, wherein the zeolite represents 1 to 3% by weight of said catalyst.

11. A catalyst system according to claim 1, said catalyst system having been prepared by a process comprising distilling an aqueous solution of phosphoric acid containing an iron compound, a compound of the metal Me, and the zeolite to remove an aqueous acidic liquor and subjecting the resultant residue to evaporation or drying, calcination, milling, and screening.

* * * * *